United States Patent [19]

Lucas

[11] Patent Number: 6,025,910
[45] Date of Patent: *Feb. 15, 2000

[54] OBJECT INSPECTION METHOD UTILIZING A CORRECTED IMAGE TO FIND UNKNOWN CHARACTERISTIC

[75] Inventor: Philip John Lucas, Lakewood, Colo.

[73] Assignee: Coors Brewing Company, Golden, Colo.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/526,897

[22] Filed: Sep. 12, 1995

[51] Int. Cl.[7] ............................. G01N 21/00; G01B 11/00
[52] U.S. Cl. ....................... 356/240; 356/428; 356/390; 382/142
[58] Field of Search .................... 356/240, 237, 356/428, 394, 390; 250/223 B, 223 R; 382/142, 141, 289, 291; 348/127, 86, 91, 94, 139, 142; 209/526, 939; 364/473.01, 468.21, 559, 571.01

[56] References Cited

U.S. PATENT DOCUMENTS

| | | |
|---|---|---|
| 3,387,551 | 6/1968 | Hughes . |
| 3,708,679 | 1/1973 | Stock et al. ........................ 250/223 R |
| 3,767,374 | 10/1973 | Iacovazzi et al. ....................... 65/165 |
| 3,886,356 | 5/1975 | Gomm et al. . |
| 4,004,904 | 1/1977 | Fergusson . |
| 4,019,819 | 4/1977 | Lodzinski ................................ 356/73 |
| 4,026,656 | 5/1977 | Kusz et al. . |
| 4,306,835 | 12/1981 | Harley ..................................... 356/43 |
| 4,332,606 | 6/1982 | Gardner . |
| 4,402,721 | 9/1983 | Ericson et al. . |
| 4,414,566 | 11/1983 | Peyton et al. .......................... 358/101 |
| 4,431,436 | 2/1984 | Lulejian .................................. 65/159 |
| 4,492,476 | 1/1985 | Miyazawa .............................. 356/428 |
| 4,494,656 | 1/1985 | Shay et al. . |
| 4,500,203 | 2/1985 | Bieringer . |
| 4,553,217 | 11/1985 | Daudt et al. . |
| 4,599,099 | 7/1986 | Jones ........................................ 65/29 |
| 4,606,746 | 8/1986 | Keller . |
| 4,608,072 | 8/1986 | Fenton ..................................... 65/79 |
| 4,614,531 | 9/1986 | Bishop et al. .......................... 65/158 |
| 4,639,263 | 1/1987 | Kulikauskas . |
| 4,649,503 | 3/1987 | Keller . |
| 4,664,521 | 5/1987 | Scotter et al. . |
| 4,675,042 | 6/1987 | Taddei-Contreras et al. ............ 65/158 |
| 4,679,075 | 7/1987 | Williams et al. . |
| 4,691,830 | 9/1987 | Ahl et al. . |
| 4,694,158 | 9/1987 | Leser ..................................... 250/223 |
| 4,762,544 | 8/1988 | Davey . |
| 4,842,411 | 6/1989 | Wood .................................... 356/376 |
| 4,915,237 | 4/1990 | Chang et al. .......................... 209/524 |

(List continued on next page.)

FOREIGN PATENT DOCUMENTS

| | | |
|---|---|---|
| 2 094 530 | 9/1982 | United Kingdom . |
| 2 179 648 | 3/1987 | United Kingdom . |

OTHER PUBLICATIONS

The Hand Book of Glass Manufacture vol. II, Fay V. Tooley, published by Books For Industry, Inc. and the Glass Industry Magazine Division of Magazines for Industry, Inc. 1974, Library of Congress No. 74–77520, PPS 961–975.

*Primary Examiner*—Robert H. Kim
*Attorney, Agent, or Firm*—Klaas, Law, O'Meara & Malkin, P.C.; Michael A. Goodwin, Esq.; William P. O'Meara, Esq.

[57] ABSTRACT

A bottle inspection method is provided which is capable of compensating for random variations in the orientation and position of objects being inspected, such as glass bottles on a conveyor. The inspection device creates an image of the object and then analyzes the image to determine the amount of variation in orientation and position. The desired measurements are made from the image and then adjusted relative to the variation previously determined. Also provided is an improved housing for the imaging devices which eliminates the need for clear panels which are prone to dirtying.

13 Claims, 6 Drawing Sheets

U.S. PATENT DOCUMENTS

| | | |
|---|---|---|
| 4,948,956 | 8/1990 | Fukuchi . |
| 4,997,769 | 3/1991 | Lundsgaard ............................. 436/66 |
| 5,187,368 | 2/1993 | Galante et al. ...................... 250/341 |
| 5,305,081 | 4/1994 | Gooch et al. ........................ 356/240 |
| 5,345,309 | 9/1994 | Wertz et al. ......................... 356/428 |
| 5,354,984 | 10/1994 | Baldwin ............................... 250/223 |
| 5,369,713 | 11/1994 | Schwartz et al. ....................... 382/8 |
| 5,414,777 | 5/1995 | van der Schaar et al. ............. 382/142 |
| 5,437,702 | 8/1995 | Burns et al. .......................... 364/473 |
| 5,510,610 | 4/1996 | Baldwin ............................. 230/223 B |
| 5,510,621 | 4/1996 | Goldman .............................. 250/343 |
| 5,592,286 | 1/1997 | Fedor ................................... 356/240 |
| 5,717,486 | 2/1998 | Burri et al. ........................... 356/240 |
| 5,734,467 | 3/1998 | Lucas .................................. 356/240 |

OBJECT INSPECTION METHOD UTILIZING A CORRECTED IMAGE TO FIND UNKNOWN CHARACTERISTIC

REFERENCE TO MICROFICHE APPENDIX

Reference is made to a Microfiche Appendix hereto, having a total of 1 microfiche and a total of 21 frames.

BACKGROUND OF THE INVENTION

The present invention relates generally to glass bottle production and, more particularly, to a glass bottle inspection apparatus adapted for use at the hot end of a glass bottle production line.

The manufacture of glass bottles begins with the preparation of raw materials. Sand and soda ash are measured in precise quantities, mixed together and conveyed to storage silos located over large melting furnaces. The mixed materials are continuously metered into the furnaces to replace molten glass which is dispensed from the furnaces after melting.

The furnaces are heated by a combination of natural gas and electricity and are operated at a temperature of over 2500 degrees Fahrenheit. The melted mixture of raw materials forms molten glass which flows from the furnaces through refractory channels, also known as forehearths, to a position over bottle forming machines.

A bottle forming machine known in the industry as an "I.S. machine" draws the glass into individual gobs and drops each gob into a blank mold. The blank mold forms a bottle preform, also referred to as a parison. The preform is transferred to a blow mold where it is blown by compressed air into a bottle. Each blow mold cavity typically contains indicia provided on a bottom wall thereof which embosses each bottle with code characters indicating the mold cavity in which it was formed.

The molds are lubricated by oil-borne carbon. The hot mold vaporizes the oil and some of the carbon immediately upon contact, leaving most of the carbon deposited upon the mold. Thus, the area around the mold is an extremely dirty environment filled with oil and carbon vapors and condensate.

An I.S. machine typically has between six and sixteen individual sections, with each section having from one to four blow mold cavities. Each section may be capable of manufacturing one to four bottles at a time. A typical eight section, triple gob, I.S. machine used in the production of beer bottles may produce 270 beer bottles per minute.

After the bottles have been blown, they are transferred from the respective blow mold cavities onto a moving conveyor belt. The bottles are positioned on the moving conveyor belt in a single line in a sequence corresponding to the sequence of the blow mold cavities in which the bottles were formed. The finished bottles transferred onto the conveyor from the blow mold are still red hot (approximately 1,000 degrees Fahrenheit). These hot bottles are conveyed by the conveyor belt through a hot end coating hood where they are chemically treated with a stannous chloride compound for strengthening. Vapors from the hot end coating hood also contribute significantly to the harsh environment found at the "hot end" of the bottle production line.

After passing through the hot end coating hood, the hot bottles are conveyed through an annealing oven or lehr where they are reheated and then cooled in a controlled manner to eliminate stresses in the glass. This annealing process typically takes from 20 to 30 minutes. The annealing process is the last process which takes place at the hot end of the production line. The portion of the production line downstream from the annealing oven is referred to as the "cold end" of the production line. In contrast to the hot end, the cold end is neither hot nor dirty. At the cold end of the production line, bottles are conveyed through a series of inspection devices. Typical prior art inspection devices include a squeezer which physically squeezes each bottle to check its sidewall strength. Another prior art cold end inspection device is referred to in the industry as a total inspection machine or T.I.M. which is sold by Emhart Glass having a business address of 123 Day Hill Road, Windsor, Conn. 06095. The total inspection machine physically engages each bottle and checks the size of the bottle neck opening and the thickness of the bottle sidewall and reads the code on the bottle bottom wall to determine the mold of origin. On a statistical sampling basis, the T.I.M. also sends bottles off line to be tested for burst strength, weighing, and measuring. Reports generated from the T.I.M. correlate bottle defects with the mold of origin. Another typical prior art inspection device is known as a "super scanner" sold by Inex, 13327 U.S. 19 North, Clearwater, Fla. 34624. The super scanner operates on each bottle on line. It initially scans a bottle, then engages and rotates the bottle approximately 90 degrees and scans it again. The super scanner uses image analysis to perform certain dimensional parameter checks of the bottle.

At both the T.I.M. and the super scanner inspection stations, defective bottles may be rejected by a cold end rejection device. After passing through the cold end inspection stations, bottles are transferred to a case packer machine, placed into a cardboard carton and conveyed to a palletizer machine for being placed in pallets. Loaded pallets are then shipped to a filling facility, such as a brewery.

A problem experienced with traditional glass bottle manufacturing operations as described above results from the fact that the bottle inspection stations are located at the cold end of the bottle production line. If a particular blow mold cavity begins producing defective bottles, e.g. as a result of a foreign object in the mold, the first defective bottle produced will not be detected until 30 to 40 minutes after its formation in the blow mold. As a result of this detection delay, the defective mold cavity will have continued to produce hundreds of defective bottles during the period between the first defective production and discovery of the first defective bottle. Furthermore, unless the defect is a defect of the type discovered by the T.I.M. machine which also identifies each bottle with a blow mold, the mold causing the problem will not be immediately apparent to the operator. As a result, the production operation must be shut down and each of the mold cavities of the I.S. machine must be inspected to detect the origin of the problem. Such shut down and inspection may be very time consuming and results in significant production loss in addition to the scrap produced by the defective mold cavity.

Locating an inspection machine at the hot end of the bottle production line is difficult for a number of reasons: (1) as a result of the elevated temperature of the bottles at the hot end of the line, any engagement of the bottles by an inspection machine as is conventional with cold end inspectors would result in deformation of the bottle surface producing an ascetically unacceptable bottle; (2) the heat of the bottles at the hot end causes the bottles to glow and would thus make reading of mold origin indicating characters on the base of the bottle extremely difficult or impossible; (3) the contaminants in the atmosphere at the hot end of the line tend to coat the surface of any optical device used to image the bottles rendering imaging difficult or impossible; (4) the extreme heat and contamination at the hot end of the line is damaging to any electronics used on inspection devices positioned at the hot end.

A solution to these problems is addressed in U.S. Pat. No. 5,437,702 of Burns et al. which is hereby specifically incorporated by reference for all that is disclosed therein. This application discloses a non-contacting optical imaging inspection system that is located at the hot end of a bottle line. The optics and electronics employed are shielded from the harsh environment at the hot end of the production line by a fluid cooled housing. Clear panels in one of the housing walls enable the imaging devices within the housing to image passing bottles without exposing the optics thereof to the harsh environment of the hot end. Fluid jets are provided adjacent to these clear panels in order to prevent contaminants from building up on the outer surface of the panels. Monitoring signals from the I.S. machine and the bottle conveyor are processed by data processing apparatus to determine the mold of origin of each bottle which is being imaged, thus obviating the need to read indicia on the surface of a glowing bottle. The image data from each bottle is analyzed to determine whether or not the bottle is defective.

Although this machine generally works well, difficulties have been experienced in determining the orientation of a bottle that is being inspected. Because the bottles cannot be physically contacted, their position relative to the inspection apparatus cannot be precisely set. Variations in the distance between a bottle being imaged and the inspection apparatus result in errors in bottle parameter measurements being taken by the inspection device. Also, because of the relative high speed of the bottle conveyor, the bottles are often bouncing when the inspection process is being carried out. Due to this bouncing, the exact orientation of a bottle when it is being inspected cannot be accurately determined. This variation in orientation also results in errors when measuring bottle parameters.

It is also been found that, despite the use of the fluid jets described above, the clear panels of the housing still occasionally become dirtied, requiring maintenance and/or resulting in degradation of performance.

SUMMARY OF THE INVENTION

The present invention is directed to an inspection device and method which is capable of compensating for random variations in the orientation of objects being inspected. The inspection device acquires an image of the object and then searches the image for a predetermined known characteristic of the object. The orientation of the image of the characteristic is then measured and compared to the actual known orientation of the characteristic to determine the deviation therebetween. The desired measurements are then made from the image of the object. These measurements are then adjusted relative to the deviation previously determined to arrive at the actual measurements of the object being inspected.

The present invention is also directed to an inspection device and apparatus which is capable of compensating for random variations in the position of objects being inspected. The inspection device adjusts the image of the object according to its location within the field of view of the imaging device to compensate for longitudinal variations in position. The inspection device compares image positioning from two imaging devices to compensate for transverse variations in position.

The inspection device also includes an improved housing for the imaging devices and associated electronics. This housing eliminates the clear panels described previously which are subject to dirtying. Openings are provided in place of these panels. The housing is maintained at a positive pressure in order to insure that no outside dirt or other contaminates infiltrate the housing through the openings. The housing may also be designed so as to minimize the required size of this opening or openings, so as to minimize the amount of pressurized fluid required to maintain the housing at a positive pressure.

BRIEF DESCRIPTION OF THE DRAWING

An illustrative and presently preferred embodiment of the invention is shown in the accompanying drawing in which.

DETAILED DESCRIPTION OF THE INVENTION

In general, the invention may pertain to a method for determining at least one unknown characteristic of an object 52. The method may include the steps of acquiring a first image of a first feature 140 of the object, acquiring a second image of a second feature 142, 144 of the object, analyzing the first image to determine the orientation of the first feature 140, analyzing the second image to determine a second image measurement and adjusting the second image measurement relative to the orientation to determine the unknown characteristic.

The invention may also include a method of determining the orientation of an object 52 which includes the steps of creating a first image of the object 52 with a first imaging device 102, analyzing the first image to determine a first orientation of the object 52 in a first plane, creating a second image of the object 52 with a second imaging device 104, analyzing the second image to determine a second orientation of the object 52 in a second plane and calculating the true orientation of the object 52 based upon the first orientation, the second orientation, and the angle between the first and second planes.

The invention may also include a method of determining at least one unknown characteristic of an object 52 which may be randomly positioned. The method may include the steps of acquiring a first image of the object 52 with a first imaging device 102 acquiring a second image of the object 52 with a second imaging device 104, comparing the first image with the second image to determine differences therebetween caused by the position of the object 52 relative to the imaging devices 102, 104, adjusting the images relative to the differences to provide at least one corrected image of the object 52 and measuring the corrected image to determine the unknown characteristic.

The invention may also pertain to an apparatus 64 for measuring at least one unknown characteristic of objects 52 being conveyed along an object pathway on a conveyor 12. The apparatus may include an enclosure 100 located adjacent the conveyor 12. The enclosure 100 is pressurized to a pressure higher than that of the surrounding atmosphere. At least one window 110 is provided in the enclosure 100. At least one image generating device 102 is located in the enclosure 100 and aimed through the window 110 at a point 50 within the object pathway. The window 110 comprises an unobstructed opening.

The invention may also pertain to an apparatus 64 for measuring at least one unknown characteristic of an object 52 being conveyed along an object pathway on a conveyor 12. The apparatus may include a first target area 134 located along the object pathway and a second target area 132 located along the object pathway. A first imaging device 102 and a second imaging device 104 are provided. A first line of sight 103 exists between the first imaging device 102 and the first target area 134. A second line of sight 105 exists between the second imaging device 104 and the second target area 132.

Having thus described the method and apparatus for measuring unknown characteristics of an object in general, further features thereof will now be specifically described.

Figure 1:
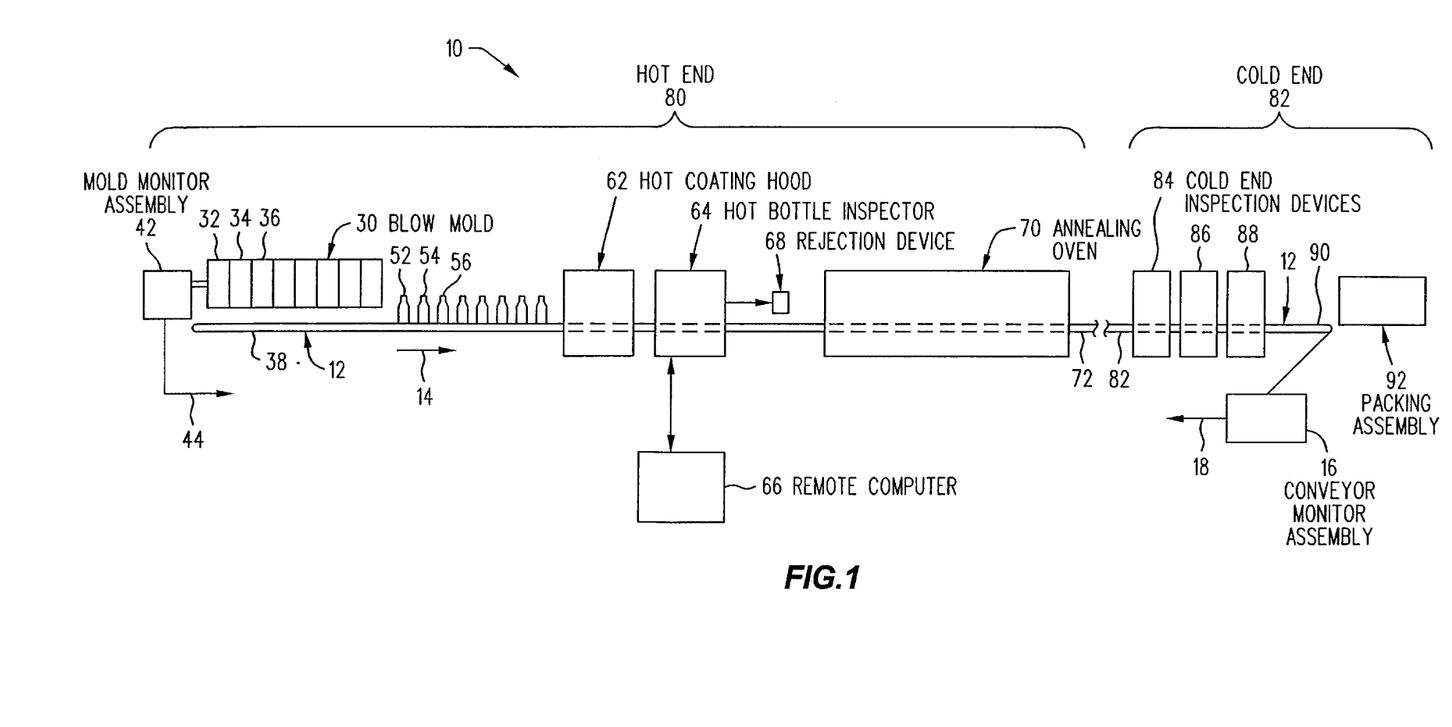
FIG. 1 is a schematic diagram of a glass bottle production line.

FIG. 1 is a schematic illustration of a glass bottle production line 10. The production line comprises a conveyor 12 which defines a bottle conveyance path. The conveyor moves bottles downstream in direction 14. A conveyor monitor assembly 16 which may be, for example, a conventional electronic encoder mounted on a conveyor motor shaft, monitors the conveying movement of conveyor 12 and produces a conveyor displacement signal 18 representative thereof. In most bottle production lines the conveyor 12 is mechanically linked to the drive mechanism of the blow mold such that conveyor speed is always directly proportional to the speed of operation of the blow mold. In such a case any device which monitors mold displacement, for example, an incremental encoder mounted on the shaft of the mold drive unit, would also indicate conveyor displacement and is to be considered a conveyor monitor.

A blow mold assembly 30 comprises a plurality of mold cavity portions 32, 34, 36, etc. The blow mold assembly 30 may comprise a portion of a conventional I.S. machine. The blow mold assembly 30 is positioned at an upstream end 38 of conveyor 12. A mold monitor assembly 42 generates a mold transfer signal 44 each time the blow mold 30 transfers bottles onto conveyor 12. Bottles 52, 54, 56, etc. are produced by mold cavity portions 32, 34, 36, etc. and are transferred to conveyor 12 in single file in a sequence corresponding to the sequence of their respective blow mold cavities of origin. The bottles 52, 54, 56 may be formed with indicia thereon indicative of the blow mold cavity of origin. The bottles 52, 54, 56, etc. are transferred onto the conveyor 12 at an elevated temperature which may be approximately 1000 degrees Fahrenheit such that the bottles are glowing.

A hot coating hood 62 is positioned at a station along the conveyor 12 a short distance downstream, e.g. 10 feet, from the blow mold 30.

A hot bottle inspection apparatus, also referred to herein as a hot bottle inspector 64, is positioned at a fixed station along the conveyor which may be a short distance, e.g. two feet, downstream from the hot coating hood 62. The hot bottle inspector 64 may thus be located in an extremely hot and dirty environment at the hot end 80 of the production line. A remote computer 66 removed from the harsh environment at the hot end of the production line is operably connected to the hot bottle inspector 64 and is accessible to a production line operator. A rejection device 68 may be positioned immediately downstream from the hot bottle inspector 64 and is operable to remove bottles from the conveyor in response to commands from the hot bottle inspector 64.

An annealing oven 70 of a conventional type may be positioned downstream of the rejection device 68 and defines, at its downstream end portion 72, the terminal end portion of the "hot end" 80 of the bottle production line 10. In a typical production line used for producing glass beer bottles, the period of time elapsing from the transfer of a bottle onto the conveyor 12 by the blow mold 30 to the exit of that bottle from the downstream end 72 of annealing oven 70 may be thirty minutes.

The portion of the production line 10 located downstream of the annealing oven exit 72 constitutes the "cold end" 82 of the production line. The cold end of the production line may comprise conventional cold end inspection devices 84, 86, 88 such as a squeezer, a T.I.M. machine, and a super inspector machine such as previously described in the "Background of the Invention" section of this application. The first of these cold end inspectors 84 may be positioned, e.g. 100 feet, downstream from the exit 72 of annealing oven 70. A conventional packing assembly 92, such as described above, may be provided downstream from the cold end inspection devices 84, 86, 88.

Figure 2:
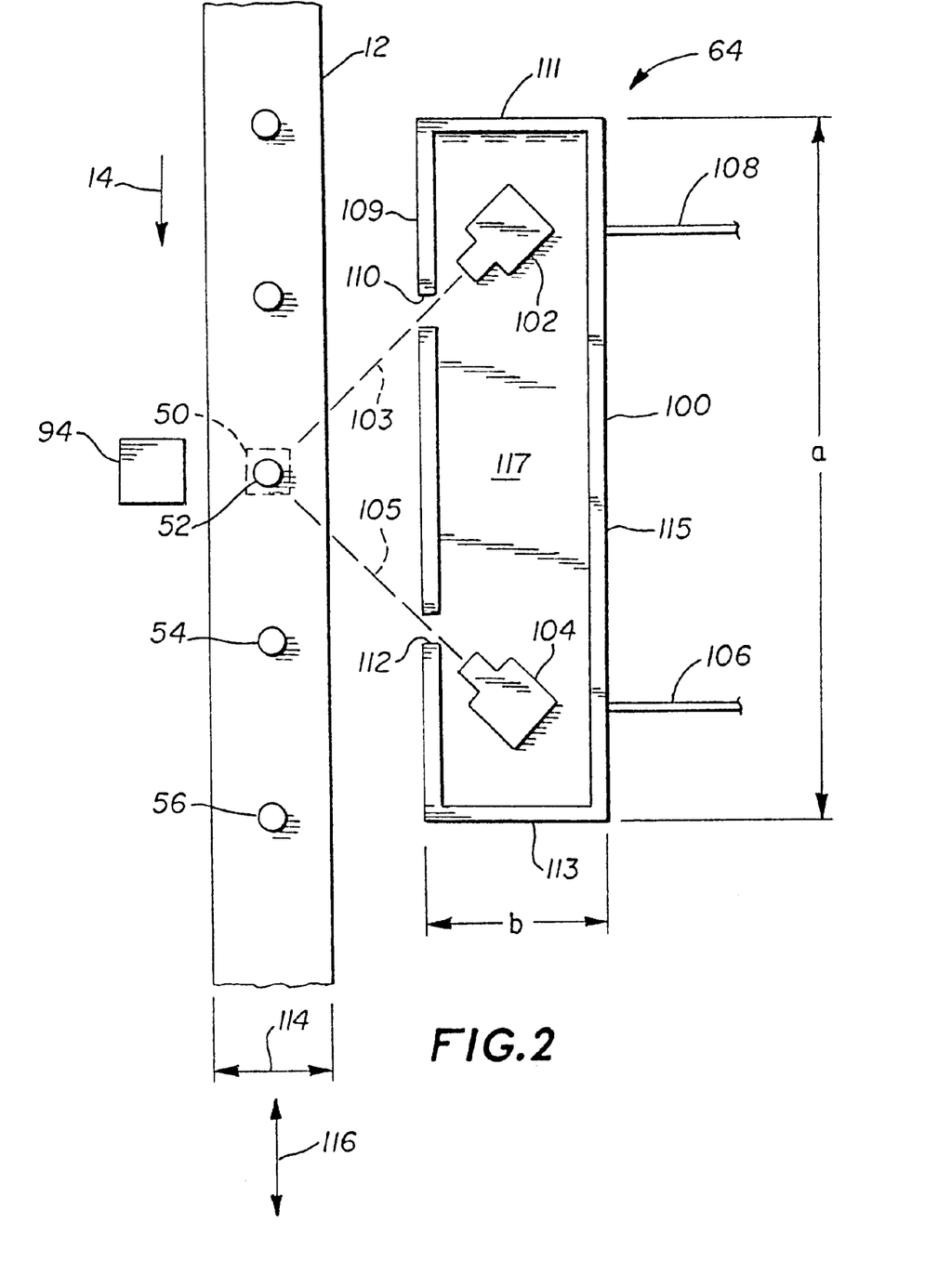
FIG. 2 is a schematic top plan view of a hot bottle inspection apparatus with its top member removed for clarity and a portion of an associated conveyor belt.

As best illustrated by FIG. 2, the hot bottle inspection apparatus 64 comprises a housing 100. This housing contains a first imaging device 102 and a second imaging device 104.

Housing 100 may comprise front wall 109, first side wall 111, second side wall 113 and rear wall 115. The housing 100 may also include a top wall member, not shown. Housing 100 may have a length "a" of about 4', a width "b" of about 2' and a height of about 4'.

A data connection 106 is provided for transmitting the images acquired by first imaging device 102 and second imaging device 104 to remote computer 66. Housing 100 may be insulated in order to withstand the intense heat of the hot end area 80. Pressurized cooling fluid is supplied to the housing 100 via fluid line 108. Fluid line 108 may supply a flow of pressurized filtered air to the housing for cooling purposes in a manner as described in the previously referenced U.S. patent application Ser. No. 111,115.

Opening 110 is provided in the front wall 109 of housing 100 to allow a line of sight 103 between the bottle 52 and first imaging device 102. Opening 112 is provided in the front wall 109 of housing 120 to allow a line of sight 105 between bottle 52 and second imaging device 104. Leaving these areas open, rather than covering them with clear panels, obviates the problem previously described regarding the panels becoming dirty. Openings 110 and 112 may each measure about 1 inch by 1 inch.

FIG. 2 shows a series of bottles such as bottles 52, 54 and 56 moving along conveyor 12 past housing 100 in the direction indicated by the arrow 14. As a bottle, such as bottle 52 in FIG. 2, moves into the target site 50, strobe light 94 is energized thus causing the imaging devices 102 and 104 to produce images of the bottle 52. The computer 66 then combines the images to arrive at a composite image as is well-known.

As previously described, the bottle forming "I.S. machine" generates signals in a well-known manner. Since the number of bottle molds within the I.S. machine is known, computer 66 can use these pulses to determine when each bottle is formed and thus when to energize the strobe light 94. Since the order of bottles on the conveyor 12 corresponds to the mold order in the I.S. machine, the computer 66 is also able to correlate acquired image data to the I.S. machine mold which formed the bottle being imaged. In this manner, bottle conditions detected by the hot bottle inspection apparatus can be correlated to a specific mold.

In one example, the I.S. machine may generate one pulse per revolution and may produce 10 bottles per revolution. In this case, computer 66 would know that 10 bottles are produced per I.S. machine pulse. The use of this type of bottle tracking system obviates the need for photosensors or other physical detectors which would be adversely affected by exposure to the harsh environment of the hot end.

In operation, cooling fluid is introduced through fluid line 108 at a rate great enough to prevent dirt and outside air from the bottle hot end 80 from entering the housing 64. The fluid entering the housing 100 maintains the interior of the housing at a pressure higher than that of the outside atmosphere. Although fluid will escape through the openings 110 and 112, new cooling fluid is introduced through fluid line 108 at a rate great enough to compensate for this escaping fluid. This arrangement eliminates the need for a discharge orifice in the housing as disclosed in the previously referenced U.S. Pat. No. 5,437,702. This arrangement also eliminates the need for the maintenance previously required for cleaning the clear panels. The cooling fluid may be in the form of compressed air.

Figure 3:
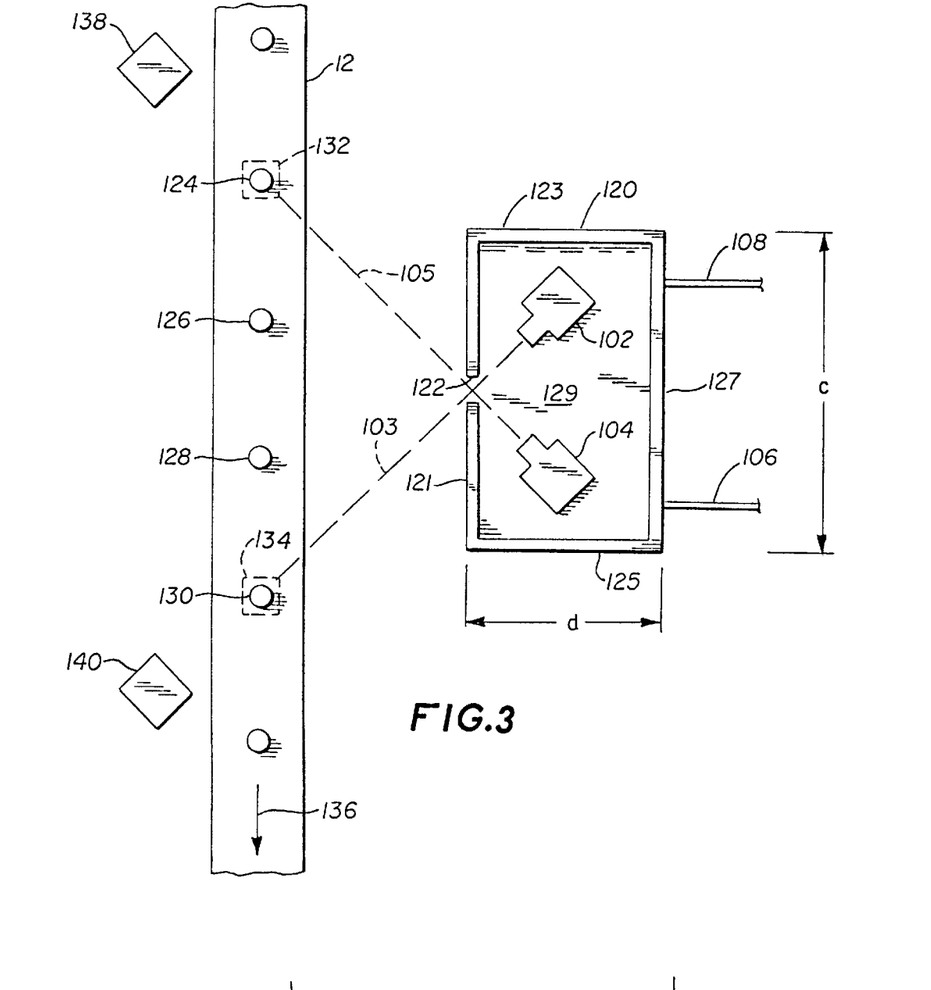
FIG. 3 is a schematic top plan view of another embodiment of the hot bottle inspection apparatus shown in FIG. 2.

FIG. 3 illustrates an alternative embodiment of the invention in which a single opening 122 is provided in a housing 120 to accommodate both lines of sight 103 and 105. Providing only one opening is advantageous since less cooling air escapes from one opening than escapes from two openings. Since less cooling air escapes, less cooling air needs to be supplied to the housing 120.

Housing 120 contains a first imaging device 102 and a second imaging device 104. Housing 120 may comprise front wall 121, first side wall 123, second side wall 125 and rear wall 127. The housing 120 may also include a top wall member, not shown. Housing 120 may have a length "c" of about 2', a width "d" of about 2' and a height of about 4'.

A data connection 106 is provided for transmitting the images acquired by first imaging device 102 and second imaging device 104 to remote computer 66. Housing 120 may be insulated in order to withstand the intense heat of the hot end area 80. Pressurized cooling fluid is supplied to the housing 120 via fluid line 108. Fluid line 108 may supply a flow of pressurized filtered air to the housing for cooling purposes as described in the previously referenced U.S. patent application Ser. No. 111,115.

An opening 122 is provided in the front wall 121 of housing 120 to allow a line of sight 103 between the first imaging device 102 and target site 134 located on conveyor 12. Opening 122 also allows a line of sight 105 between second imaging device 104 and target site 132 located on the conveyor 12. The imaging devices 102 and 104 are configured within housing 120 so that their lines of sight 103 and 105 cross in the vicinity of the opening 122 as shown in FIG. 3. Configuring the imaging devices in this manner allows the use of one relatively small opening 122 in housing 120, thus reducing the loss of cooling air from housing 120.

Because of the configuration of imaging devices 102 and 104 described above, each imaging device will image a different bottle at any given time. In order to combine the proper images from imaging devices 102 and 104, the remote computer 66 stores image data for a particular bottle from imaging device 104 until the same bottle moves into a position where it is imaged by imaging device 102. The computer then assembles the image data from the two imaging devices 102 and 104 to obtain complete data for each bottle.

FIG. 3 shows a series of bottles such as bottles 124, 126, 128, and 130 moving along conveyor 12 past housing 120 in the direction indicated by the arrow 136. As a bottle, such as bottle 124 in FIG. 3, moves into the target site 132, strobe light 138 is energized thus causing imaging device 104 to produce an image of the bottle 124. This image is stored by the computer 66 until the bottle 124 moves into the target site 134 and strobe light 140 is energized, thus causing imaging device 102 to produce an image of the bottle 124. The computer then combines the stored image from imaging device 104 with the newly acquired image from imaging device 102 to arrive at a complete image of bottle 124. This process is repeated for each bottle conveyed by the conveyor 12. Bottles are tracked by the computer 66 using I.S. machine pulses in a manner as previously described.

Opening 122 may measure about 1" inch by 1 inch. In operation, cooling fluid is introduced through fluid line 108 at a rate great enough to prevent dirt and outside air from the bottle hot end 80 from entering the housing 120. The fluid entering the housing 120 maintains the interior of the housing at a pressure higher than that of the outside atmosphere. Although fluid will escape through the opening 122, new cooling fluid is introduced through fluid line 108 at a rate great enough to compensate for this escaping fluid. It has been found that supplying cooling fluid in the form of compressed air at a rate of about 2 standard cubic feet per minute is sufficient given the size of the housing 120 and the opening 122 as described above. The compressed air may be supplied to housing 120 at a temperature of about 30 degrees celsius.

With respect to either housing 100 or housing 120, the imaging devices 102 and 104 may be located so that the center of their lenses are vertically aligned with the plane of the top of the conveyor 12. This results in the imaging devices being located substantially below the plane of the conveyor. Since heat rises, this location is cooler and thus less damaging to the imaging devices. This location also allows the plane of the conveyor to be conveniently used as a reference plane when analyzing bottle image data.

In another embodiment, the hot bottle inspection system housing may actually comprise two separate housing units, one for each imaging device 102, 104. This embodiment may be configured as shown in FIG. 2 except that a separate housing is provided for each imaging device 102, 104. These housings may each have a length of about 6", a width of about 6" and a height of about 6" and be otherwise constructed in substantially the same manner as the previously described housings 100, 120. The use of two separate housings may make personnel access to the bottle line easier in some situations.

Correction for Orientation

The general technique of imaging of bottles onto photoelectric devices such as CCDs (charge couple devices) and the subsequent analysis of the data signal to measure various bottle parameters is well known in the art. It has been found, however, that measuring bottles at the hot end 80 of a bottle production line 10 presents problems which have not previously been solved.

As a result of the elevated temperature of the bottles at the hot end 80 of the production line 10, any engagement of the bottles by an inspection machine, as is conventional with cold end inspectors, would result in deformation of the bottle surface producing an ascetically unacceptable bottle. This, along with the relatively high speed of bottle production line conveyors means that the bottles are often bouncing when a hot end inspection process is being carried out. Due to this bouncing, the exact orientation of a bottle when it is being inspected cannot be accurately determined.

The present invention overcomes this difficulty by first analyzing the bottle image to find a known feature of the bottle. The orientation of this feature, and thus the entire bottle, is then determined. The desired bottle measurements are then made and adjusted relative to the orientation of the known feature. This allows true measurements to be achieved even on randomly oriented bottles, such as bouncing bottles.

One example of a particular physical parameter which may be determined by the imaging device of the present invention is the degree to which the sidewalls of a bottle are perpendicular to its base.

Figure 4:
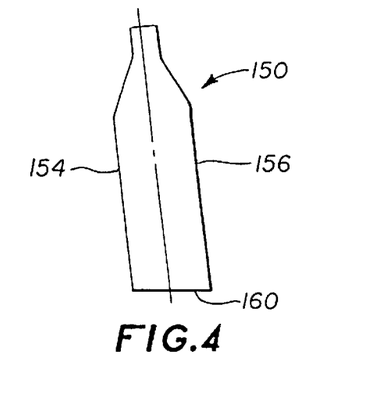
FIG. 4 is a schematic front elevation view of a defective bottle.
Figure 5:
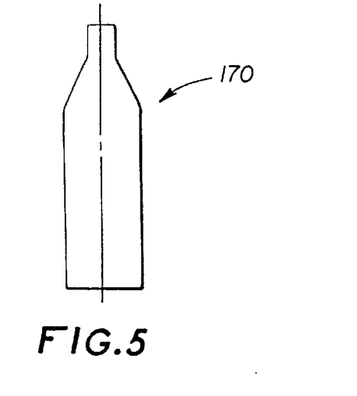
FIG. 5 is a schematic front elevation view of a non-defective bottle.

FIG. 4 schematically illustrates a bottle 150, the sidewalls 154, 156 of which are not perpendicular to its base 160. This defective condition is commonly referred to as "lean" and bottles exhibiting this condition are commonly referred to as "leaners". It should be noted that the lean depicted in FIG. 4 has been greatly exaggerated for purposes of illustration. FIG. 5 shows a non-defective bottle 170 exhibiting no perceptible lean.

The lean measured by the hot bottle inspection apparatus 64 may be compared with pre-determined values and any bottle having parameters exceeding a fixed tolerance from this value is determined by the system to be defective. It is noted, however, that, in the case of leaners, detecting even a slight lean that is within tolerance can be useful to bottle line process control. Leaners generally occur when the bottle formation temperature becomes too high. This high temperature causes the glass to be too soft and, thus, leaners occur. Accordingly, early detection of in-tolerance leaners can provide the bottle line operators with information indicating that the bottle formation process is becoming too hot. Adequate corrective action can then be taken to prevent further overheating and the occurrence of reject-level leaners.

Referring again to FIG. 2, it can be seen that first imaging device 102 and second imaging device 104 image the bottle 52 from different directions. This ensures that a leaner will be detected even if it is leaning directly toward or away from one of the imaging devices. In such a case, the other imaging device would still detect the lean.

Figure 6:
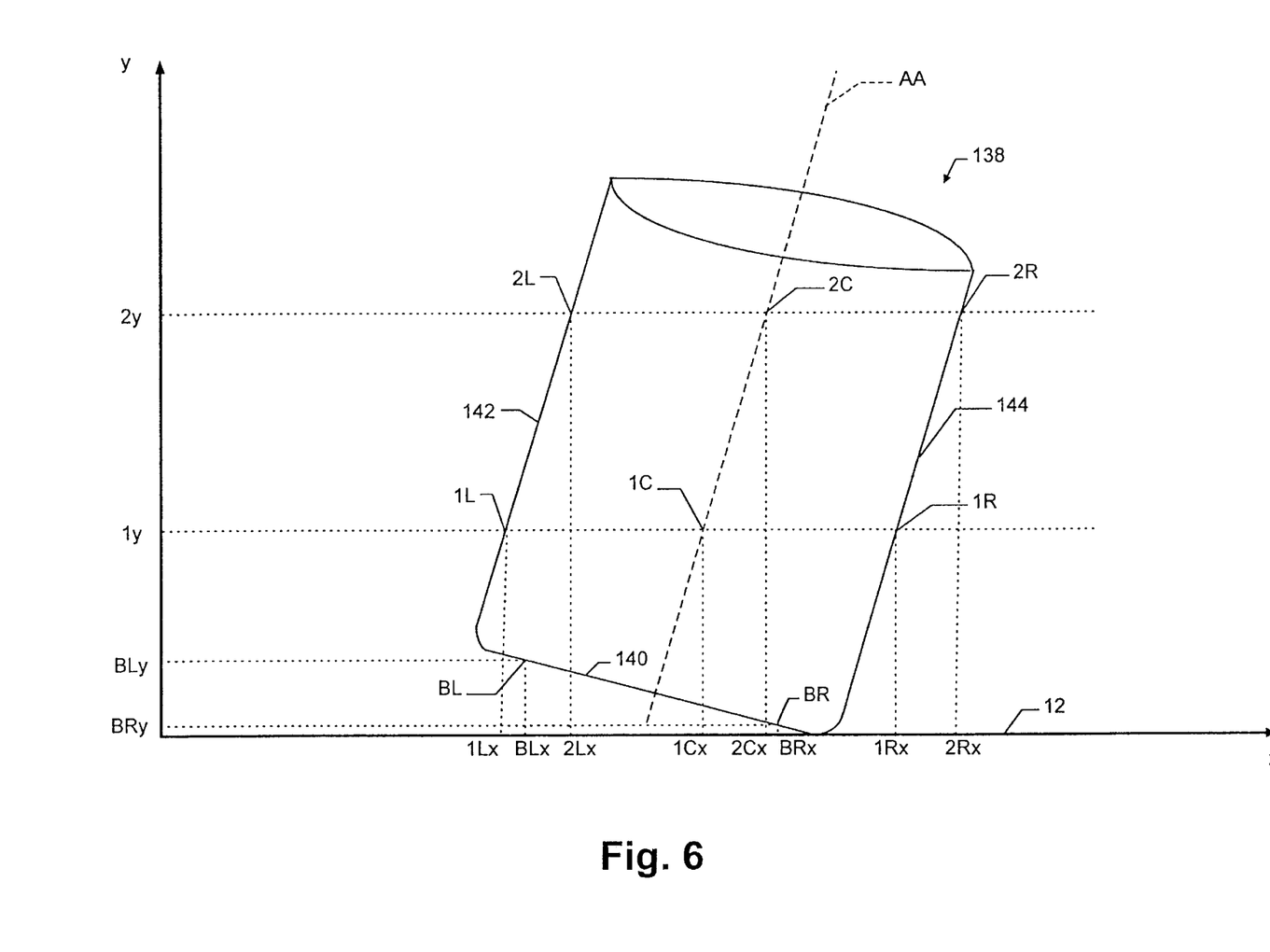
FIG. 6 is a schematic front elevation view illustrating the process used to analyze a bottle that is randomly oriented.

The method employed to compensate for bottle orientation will now be described in detail. FIG. 6 illustrates an image of a bottle 138 generated, for example, by first imaging device 102. The bottle 138 was imaged while it was bouncing and thus is shown in a random orientation in FIG. 6.

Bottle lean may be characterized by the deviation of the center line AA of a bottle from vertical. In other words, deviation may be described as the difference between the horizontal location of the bottle centerline AA near the base 140 of the bottle and the horizontal location of the bottle centerline AA near the top of the bottle. If these horizontal locations are identical, then the bottle exhibits no lean. If they are different, however, then the bottle is a leaner and the magnitude of this horizontal difference characterizes the amount of lean.

Figure 7:
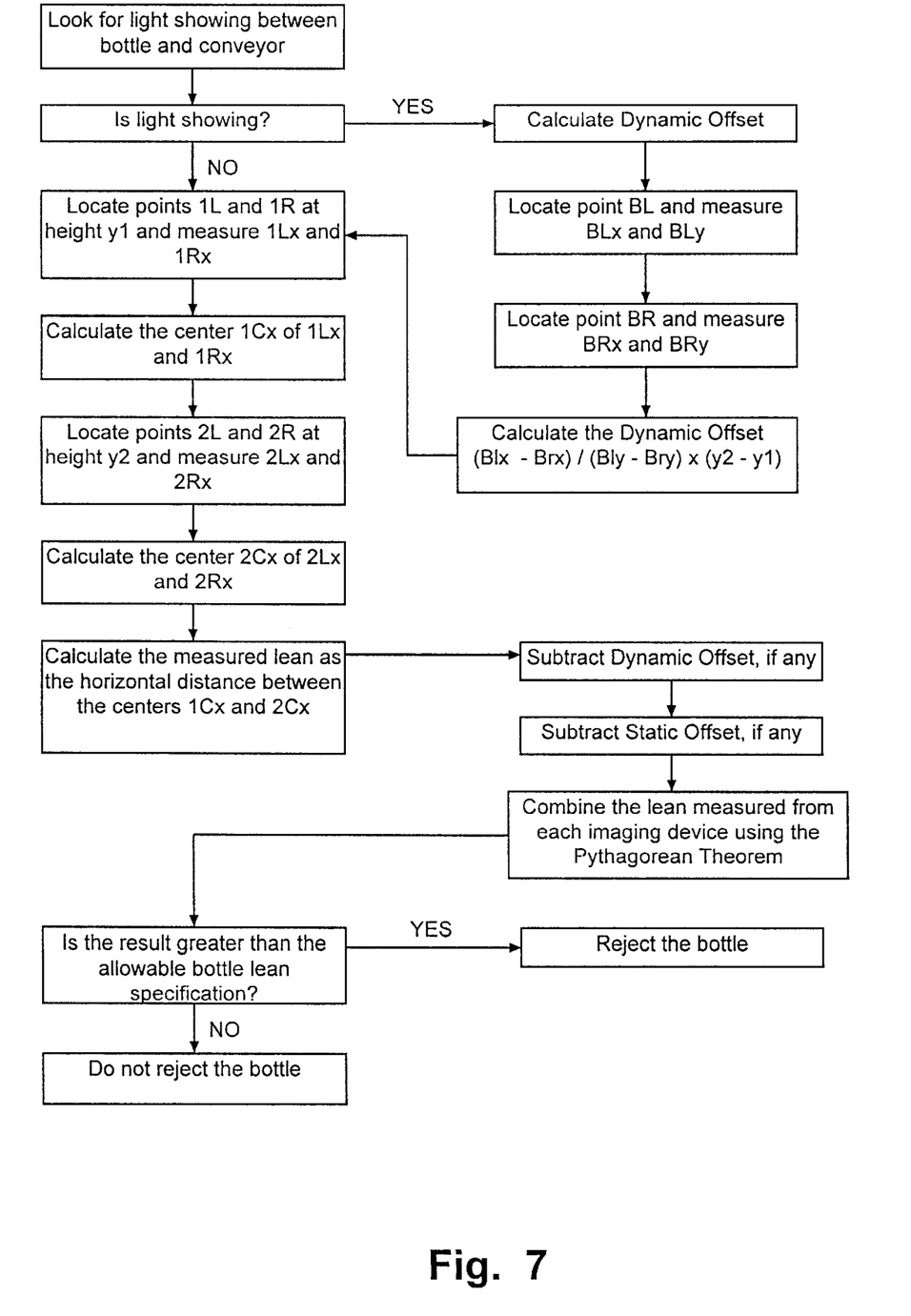
FIG. 7 is a flow chart illustrating the steps taken to compensate for randomly oriented bottles.

A specific method for measuring lean will now be described in detail with reference to FIG. 6. FIG. 7 is a block diagram illustrating this method.

First, the image is analyzed to determine if there is any light showing beneath the base 140 of the bottle image 138. If no light is showing, this means that the bottle is setting flat on the conveyor 12 and is not bouncing. If light is showing, as in the case of FIG. 6, this means that the bottle is not setting flat on the conveyor and compensation must be made for the orientation of the bottle due to bouncing.

If the bottle is bouncing, then the "dynamic offset" is calculated. The dynamic offset is the amount of measured lean caused by the orientation of the bottle. To calculate the dynamic offset, the base 140, left edge 142 and right edge 144 of the bottle are first located. Next a point "BL" is located on the base 140 of the bottle. The point BL is defined as a point located along the base 140 of the bottle at a predetermined distance in from the left edge 142 of the bottle. It is not desirable to use the actual corner of the bottle for the point BL since bottle corners are often rounded, making a precise location in this area difficult.

A point "BR" is then located on the base 140 of the bottle. The point BR is defined as a point located along the base 140 of the bottle at a predetermined distance in from the right edge 144 of the bottle. Both of the points BL and BR may be located the same distance in from their respective edges. This distance may, for example, be about 0.5 inches.

The dynamic offset is then calculated as:

$$(BLx-BRx)/(BLy-BRy) \times (2y-1y)$$

where BLx is the location along the x-axis of point BL, BRx is the location along the x-axis of point BR, BLy is the location along the y-axis of point BL, BRy is the point along the y-axis of point BR and 2y and 1y are predetermined heights above the plane of the conveyor 12 used to measure bottle lean as further described below.

After the dynamic offset is calculated (or if no dynamic offset is calculated because the bottle was not bouncing when imaged), points 1L and 1R are located. Point 1L is the point where the left edge 142 of the bottle image is found at a predetermined height 1y above the plane of the conveyor 12. Point 1R is the point where the right edge 144 of the bottle image is found at the same height 1y above the plane of the conveyor 12. For purposes of example, the height 1y may be about 1.25 inches.

The location of the horizontal center 1C of points 1L and 1R is then calculated as the point having a y location equal to 1y and an x location equal to:

$$(1Lx+1Rx)/2$$

where 1Lx is the location along the x-axis of point 1L and 1Rx is the location along the x-axis of point 1R.

Next, points 2L and 2R are located. Point 2L is the point where the left edge 142 of the bottle image is found at a predetermined height 2y above the plane of the conveyor 12. Point 2R is the point where the right edge 144 of the bottle image is found at the same height 2y above the plane of the conveyor 12. For purposes of example, the height 2y may be about 6 inches.

The location of the horizontal center 2C of points 2L and 2R is then calculated as the point having a y location equal to 2y and an x location equal to:

$$(2Lx+2Rx)/2$$

where 2Lx is the location along the x-axis of point 2L and 2Rx is the location along the x-axis of point 2R.

The points 1Cx and 2Cx lie along the centerline AA of the bottle and, thus, together define the centerline AA. The measured lean is then calculated as the difference in horizontal location of the center points 1Cx and 2Cx:

$$2Cx-1Cx$$

Next, the dynamic offset, if any, is subtracted from the measured lean to arrive at the true bottle lean. Since the dynamic offset represents the lean attributable to the bottle's orientation on the conveyor, subtracting out this lean will result in the lean that is inherent in the bottle itself.

The above method is carried out for each of the imaging devices 102 and 104. The bottle lean calculated for each imaging device is then combined to arrive at a combined true bottle lean as will now be described.

Imaging devices 102 and 104 are arranged such that their lines of sight 103 and 105, respectively cross at right angles to one another, FIGS. 2 and 3. Since each imaging device can only measure lean perpendicular to its line of sight, this means that the lean measured by imaging device 102 will always be at a right angle to the lean measured by imaging device 104. Since two right angle component of the true lean are known, the Pythagorean theorem can be used to calculate the combined true lean as:

$$(L1^{2+L22})^{1/2}$$

where L1 is the true lean calculated based on the image from first imaging device 102 and L2 is the true lean calculated based on the image from second imaging device 104.

The combined true bottle lean is then compared to the allowable specification. If the combined true lean exceeds the allowable lean, then the bottle is rejected by rejection device 68. If, however, the combined true lean is within acceptable limits, the bottle is allowed to continue on the conveyor 12 toward the cold end 82 of the bottle production line.

The combined true lean information may be made available to the bottle production line operators even in cases where the lean is found to be within allowable limits. This allows the operators to observe and to react to any trend in the combined true lean measurements. Increasing lean, for example, may indicate that the bottle forming process is becoming too hot. An operator, observing such an increase, can take appropriate steps to lower the temperature of the bottle forming process before bottles having rejection level defects are formed. Such feedback of bottle lean information, thus, allows avoidance of potential rejects. Alternatively, a computer may be used to observe and automatically react to such trend information.

In addition to the dynamic offset described above, a static offset may also be subtracted from the measured lean to arrive at the true bottle lean. Static offset is the offset measured when an in-specification bottle is placed flat on the conveyor 12, while the conveyor is not moving. Static offset accounts for errors in the hot bottle inspection system itself that do not change from bottle to bottle. For example, static offset may account for any misalignment between the imaging devices 102, 104 and the bottle conveyor 12.

Static offset may also account for lens aberration. Each imaging device 102, 104 contains a lens as is well-known. All lenses display some degree of aberration, or distortion in some areas of the lens. Static offset accounts for such aberration. Subtracting the static offset in this manner also allows less expensive lenses to be employed. Less expensive lenses tend to exhibit more aberration than do more costly lenses. Since this aberration is static and predictable, however, using a static offset, as described above, allows less expensive lenses to be used while still ensuring that accurate bottle lean information can be obtained.

Although the bottle inspection method has been described with respect to obtaining two center points 1C and 2C, it is noted that a greater number of points can be evaluated if desired. If a greater number of points are used, the lean can be calculated by taking the average of the individual leans calculated between each of the points.

Using a greater number of points also facilitates the detection of other bottle abnormalities such as bulges. If a bulge exists in the sidewall of a bottle, this will cause the center point at this location to be offset from the other center points thus indicating that a problem exists in this area.

In addition to bottle lean information, the procedure described above may also be used to measure actual bottle dimensions at various locations. Once the bottle lean is known, the true bottle width, e.g., may be calculated using trigonometry. An example of such a calculation is described below with respect to FIG. 6.

For purposes of this example, the "lean angle" is the angle formed between the base 140 of the bottle and the conveyor 12. The lean angle may be calculated using any number of trigonometric functions and the bottle measurement data which has been collected as previously described. The lean angle may, for example, be calculated as follows:

$$\text{lean angle}=\tan^{-1}((BLy-BRy)/(BLx-BRx))$$

Once calculated, the lean angle may then be used to derive the true bottle dimensions from the measured image data. For example, the true bottle width at the point 1L may be calculated as follows:

$$\text{true width}=\cos(\text{lean angle})\times(1Lx-1Rx)$$

Other true bottle dimensions may be calculated in a similar manner once the lean angle is known.

Correction for Longitudinal Misalignment

It has been found that the position of a bottle such as bottle 52 on conveyor 12 can vary from bottle to bottle. This is because, as bottles are placed onto the conveyor by the blow mold 30, they are not always placed in exactly the same position on the conveyor. Accordingly, the position of a particular bottle can vary both in a transverse direction 114 (in a direction perpendicular to the direction of conveyor movement) and also in a longitudinal direction 116, perpendicular to the transverse direction as shown in FIG. 2.

Referring to FIG. 2, when a bottle 52 is perfectly aligned longitudinally, it will be located at the target site 52 when the strobe 94 is energized. In this case, the bottle 52 will be longitudinally equidistant from the imaging devices 102, 104. When a bottle 52 varies in longitudinal direction 116, however, it will either be downstream (in the direction of the arrow 14) or upstream (in the direction opposite the arrow 14) of the target site 50 when the strobe 94 is energized. If the bottle 52 is downstream, it will be closer to imaging device 104 and further from imaging device 102. Conversely, if the bottle 52 is upstream, it will be closer to imaging device 102 and further from imaging device 104.

When the bottle 52 is closer to one imaging device than the other, the image of the bottle acquired by the closer imaging device will be larger than the image of the bottle acquired by the further imaging device. When this condition is detected by the computer 66, the bottle being imaged is longitudinally misaligned. By measuring the amount of difference in bottle image size, the computer 66 can determine the amount of longitudinal misalignment and correct the image size accordingly.

Correction for Transverse Misalignment

Figure 8:
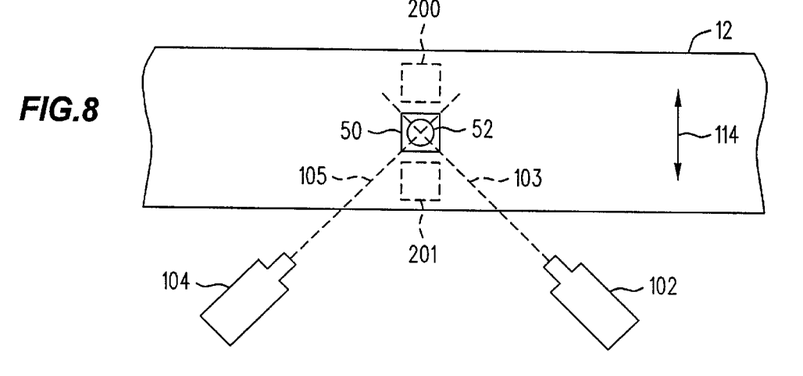
FIG. 8 is a plan view of the imaging device of FIG. 2 schematically illustrating a bottle that is transversely misaligned.

Referring to FIGS. 2 and 8, when a bottle 52 is perfectly aligned in a transverse direction 114, it will be located at the target site 50 when the strobe 94 is energized. When a bottle 52 varies in transverse direction 114, however, it will either be closer to, e.g., position 202, or further from, e.g., position 200, the imaging devices 102, 104, FIG. 8.

Figure 9A:
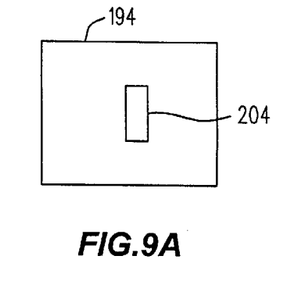
FIGS. 9A–9C schematically illustrate a bottle image from a first imaging device, a bottle image from a second imaging device and a combined bottle image, respectively, when the bottle being imaged is transversely misaligned closer to the imaging devices.
Figure 9B:
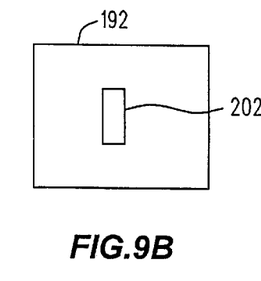
Figure 9C:
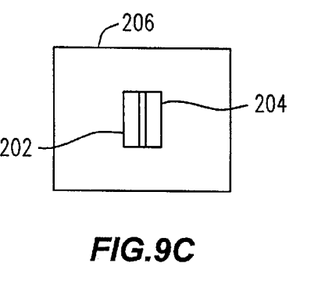
Figure 10A:
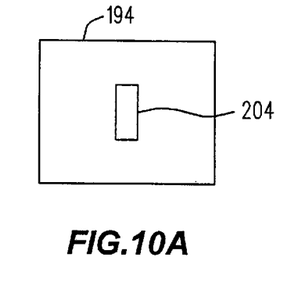
FIGS. 10A–10C schematically illustrate a bottle image from a first imaging device, a bottle image from a second imaging device and a combined bottle image, respectively, when the bottle being imaged is transversely aligned.
Figure 10B:
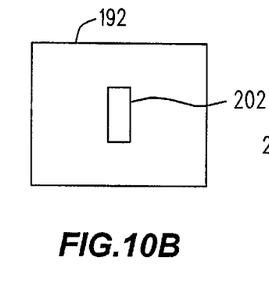
Figure 10C:
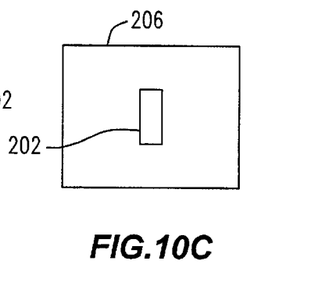

FIGS. 9A–11A schematically illustrate the image 194 acquired by the imaging device 104 which includes the bottle image 204. FIGS. 9B–11B illustrate the image 192 acquired by the imaging device 102 which includes the bottle image 202. To determine transverse location, the computer 66 combines the image 192 and the image 194 from the imaging devices 102, 104 into one image 206, FIGS. 9C–11C. If the bottle 52 is perfectly aligned transversely, as shown in FIGS. 2 and 10, the image of the bottle acquired from each imaging device 102, 104 will overlap. The combined image will, thus result in only one bottle image as seen in FIG. 10C.

If, however, the bottle 52 is transversely misaligned closer to the imaging devices 102, 104, e.g. at the position 202, FIG. 8, the bottle image 202 acquired by imaging device 102 will be shifted to the left (since the bottle has shifted to the left in the field of view of imaging device 102). This is best illustrated in FIG. 9B.

In a similar manner, the bottle image 204 acquired by imaging device 104 will be shifted to the right (since the bottle has shifted to the right in the field of view of imaging device 104). This is best illustrated in FIG. 9A.

In such a misaligned configuration, the combined image 206, FIG. 9C will result in the individual bottle images 202, 204 not overlapping. In other words, the edges of the bottle images 202, 204 acquired from imaging devices 102, 104 will not overlap. Specifically, the bottle image 202 acquired by the imaging device 102 will be shifted to the left relative to the bottle image 204 acquired by the imaging device 104 as shown in FIG. 9C.

Figure 11A:
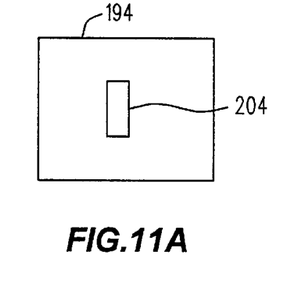
FIGS. 11A–11C schematically illustrate a bottle image from a first imaging device, a bottle image from a second imaging device and a combined bottle image, respectively, when the bottle being imaged is transversely misaligned further from the imaging devices.
Figure 11B:
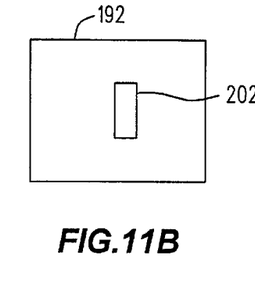

If the bottle 52 is transversely misaligned further from the imaging devices 102, 104, e.g., at the position 200, FIG. 8, the bottle image 202 acquired by imaging device 102 will be shifted to the right (since the bottle has shifted to the right in the field of view of imaging device 102). This is best illustrated in FIG. 11B.

In a similar manner, the bottle image 204 acquired by imaging device 104 will be shifted to the left (since the bottle has shifted to the left in the field of view of imaging device 104). This is best illustrated in FIG. 11A.

Figure 11C:
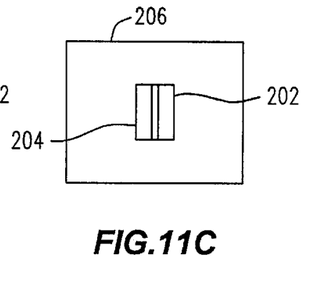

In such a misaligned configuration, the combined image 206, FIG. 11C will result in the individual bottle images 202, 204 not overlapping. In other words, the edges of the bottle images 202, 204 acquired from imaging devices 102, 104 will not overlap. Specifically, the bottle image 202 acquired by the imaging device 102 will be shifted to the right relative to the bottle image 204 acquired by the imaging device 104 as shown in FIG. 11C.

Accordingly, the computer 66 can detect that a transverse misalignment condition exists and can determine in which direction the misalignment occurs. By measuring the distance between the bottle images 202, 204, the computer 66 can also measure the amount of misalignment. Once the amount of misalignment is known, the computer 66 may align the images 202, 204 and adjust the size of the image to compensate for the transverse misalignment. In other words, if the computer 66 detects that the bottle 52 is transversely misaligned further from the imaging devices 102, 104, e.g. at the position 200, the combined bottle image may be enlarged in accordance with the amount of transverse misalignment. In a similar manner, if the computer 66 detects that the bottle 52 is transversely misaligned closer to the imaging devices 102, 104, e.g. the position 201, the combined bottle image may be reduced in accordance with the amount of transverse misalignment.

Upon initial start-up of the inspection apparatus 64, it may be calibrated by running bottles of known dimensions and characteristics through the inspection apparatus. The computer 64 can then correlate the actual size of these bottles to the size of their images generated by the inspection apparatus 64. The computer 66 may then use this relationship to measure characteristics of unknown bottles as described above.

Although the above methods for correction of orientation and position have been described with respect to bottle inspection, these methods could be used for any inspection task in which the objects being inspected are not uniformly oriented and/or positioned.

The software code for accomplishing the above methods is set forth in the previously referenced Microfiche Appendix and forms a part of this disclosure.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A method of determining at least one unknown characteristic of an object, comprising the steps of:

(a) acquiring a first image of a first feature of said object;

(b) acquiring a second image of a second feature of said object;

(c) analyzing said first image to determine the orientation of said first feature;

(d) analyzing said second image to determine a second image measurement;

(e) adjusting said second image measurement relative said orientation to determine said at least one unknown characteristic.

2. The method of claim 1 wherein said object is a bottle.

3. The method of claim 2 wherein said first feature is the bottom of said bottle.

4. The method of claim 2 wherein said unknown characteristic is bottle lean.

5. The method of claim 2 wherein said second feature includes the edges of said bottle.

6. The method of claim 5 wherein said step of analyzing said second image includes locating said edges and measuring the distance therebetween at at least two locations.

7. A method of determining at least one unknown characteristic of an object which may be randomly positioned, comprising the steps of:
   (a) acquiring a first image of said object with a first imaging device;
   (b) acquiring a second image of said object with a second imaging device;
   (c) comparing said first image with said second image to determine differences therebetween caused by the position of said object relative to said imaging devices;
   (d) adjusting said images relative said differences to provide at least one corrected image of said object;
   (e) measuring said corrected image to determine said unknown characteristic.

8. The method of claim 7 wherein said object is moving on a conveyor along a movement path when said images are acquired.

9. The method of claim 8 wherein said first imaging device has a first line of sight, said second imaging device has a second line of sight and said first line of sight and said second line of sight intersect at a target area located generally in said movement path.

10. The method of claim 9 wherein said differences are caused by said object being misaligned with said target area in a direction parallel to said movement path.

11. The method of claim 9 wherein said differences are caused by said object being misaligned with said target area in a direction transverse to said movement path.

12. The method of claim 7 wherein said differences comprise a difference between the size of said first image of said object and the size of the second image of said object.

13. The method of claim 7 wherein said differences comprise a difference between the position of said first image of said object and the position of said second image of said object.

* * * * *